United States Patent

Herrmann et al.

Patent Number: 5,808,122
Date of Patent: Sep. 15, 1998

[54] ORGANOMETALLIC COMPOUND

[75] Inventors: Hans-Friedrich Herrmann, Dornheim; Frank Küber, Oberursel; Wolfgang Anton Herrmann, Freising; Markus Morawietz, Hanau, all of Germany

[73] Assignee: Hoechst Aktiengesellschaft, Germany

[21] Appl. No.: 646,876

[22] Filed: May 8, 1996

[30] Foreign Application Priority Data

May 8, 1995 [DE] Germany ............... 195 16 801.1

[51] Int. Cl.⁶ ............... C07F 11/00; C07F 17/00
[52] U.S. Cl. ............... 556/58; 556/57; 502/117; 502/155; 526/161; 526/943
[58] Field of Search ............... 556/57, 58

[56] References Cited

U.S. PATENT DOCUMENTS

| | | | |
|---|---|---|---|
| 5,272,236 | 12/1993 | Lai et al. | 526/348.5 |
| 5,278,272 | 1/1994 | Lai et al. | 526/348.5 |
| 5,320,996 | 6/1994 | Carney et al. | |
| 5,391,789 | 2/1995 | Rohmann et al. | 556/11 |
| 5,529,966 | 6/1996 | Luciani et al. | 502/117 |

FOREIGN PATENT DOCUMENTS

| | | |
|---|---|---|
| 351 392 | 5/1989 | European Pat. Off. |
| 528 287 | 8/1992 | European Pat. Off. |
| 94/11410 | 5/1994 | WIPO |

OTHER PUBLICATIONS

Halterman, Ronald L., "Synthesis and Applications of Chiral cyclopentadienylmetal Complexes" Chem. Rev. 92, pp. 965–994, 1992.

Wolfgang A. Herrmann, First amido-functionalized ansa-molybdenocene-type complexes, Journal of Organometallic Chemistry 497 (1995) C4–C6, Jan. 1995.

*Primary Examiner*—David W. Wu
*Attorney, Agent, or Firm*—Connolly and Hutz

[57] ABSTRACT

The invention relates to an organometallic compound of the formula I

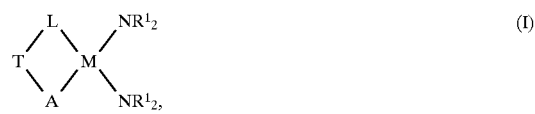

where M is chromium, molybdenum or tungsten, L is a cyclopentadienyl ligand, T is a bridge, A is a cyclopentadienyl ligand or an electron donor and $R^1$ are, independently of one another, identical or different $C_1$–$C_{20}$-hydrocarbon radicals or hydrogen. The organometallic compound is suitable as a catalyst component for olefin polymerization.

14 Claims, No Drawings

ORGANOMETALLIC COMPOUND

The present invention relates to an organometallic compound which can be used very advantageously as a catalyst component, e.g. for the preparation of polyolefins or metathesis for ring-opening polymerization (ROMP). Metallocenes and semi-sandwich complexes are not only of great interest for polymerization, oligomerization or metathesis of olefins, but can also be used as hydrogenation, epoxidation, isomerization and C—C coupling catalysts (Chem. Rev. 1992, 92, 965–994).

Organometallic compounds containing Cr, Mo or W and having π ligands can be used as polymerization catalysts (WO 94/11410). However, the preparation of such compounds proves to be difficult.

It is an object of the invention to provide a new organometallic compound which is suitable for olefin polymerization. It has surprisingly been found that a new organometallic compound is obtained directly by reacting a metal tetramide of the 6th transition group of the Periodic Table of the Elements (Cr, Mo, W) with a ligand system without addition of a base such as butyllithium.

The present invention accordingly provides an organometallic compound of the formula I

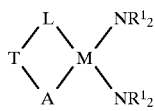 (I)

where M is chromium, molybdenum or tungsten, L is a π ligand, T is a bridge, A is a π ligand or another electron donor and $R^1$ are, independently of one another, identical or different $C_1$–$C_{20}$-hydrocarbon radicals or hydrogen.

L is preferably a substituted or unsubstituted cyclopentadienyl group, T is preferably $[R^2{}_2B]_n$, where B is carbon, silicon, germanium or tin and the radicals $R^2$ are identical or different and are each hydrogen or a $C_1$–$C_{30}$-hydrocarbon radical such as $C_1$–$C_{10}$-alkyl or $C_6$–$C_{14}$-aryl, and n is equal to 1, 2, 3 or 4. A is a π ligand such as a substituted or unsubstituted cyclopentadienyl group or another electron donor such as O, $PR^3$, S or $NR^3$, where $R^3$ is hydrogen or a $C_1$–$C_{30}$-hydrocarbon radical such as $C_1$–$C_{10}$-alkyl or $C_6$–$C_{14}$-aryl.

$R^1$ are preferably identical and are each hydrogen or a $C_1$–$C_{20}$-hydrocarbon radical such as $C_1$–$C_{10}$-alkyl or $C_6$–$C_{16}$-aryl.

Examples of substituted cyclopentadienyl groups are:
tetramethylcyclopentadienyl, methylcyclopentadienyl, methyl-tert-butylcyclopentadienyl, tert-butylcyclopentadienyl, isopropylcyclopentadienyl, dimethylcyclopentadienyl, trimethylcyclopentadienyl, trimethylethylcyclopentadienyl, 5-phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthylindenyl, 2-methyl-4-isopropylindenyl, benzoindenyl, 2-methyl-4,5-benzoindenyl, 2-methyl-α-acenaphthindenyl, 2-methyl-4,6-diisopropylindenyl, fluorenyl, 4-methylfluorenyl or 2,7-di-tertbutylfluorenyl.

Examples of preferred bridges T are:
dimethylsilanediyl, methylphenylsilanediyl, diphenylsilanediyl, dimethylgermanediyl, 1,2-tetramethyldisilanediyl, 1,2-ethylidene, 1,2-propylidene, 1,2-butylidene, 1,3-propylidene, 1,4-butylidene.

Examples of preferred structural elements A are:
tert-butylamido, cyclohexylamido, phenylamido, 2,6-diisopropylphenylamido, 2,6-di-tert-butylphenylamido, cyclododecylamido, —O—, cyclopentadienyl, indenyl, fluorenyl, cyclopentadienyl, tetramethylcyclopentadienyl, methylcyclopentadienyl, methyl-tert-butylcyclopentadienyl, tert-butylcyclopentadienyl, isopropylcyclopentadienyl, dimethylcyclopentadienyl, trimethylcyclopentadienyl, trimethylethylcyclopentadienyl, phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-isopropylindenyl, benzoindenyl, 2-methyl-4,5-benzoindenyl, 2-methyl-α-acenaphthindenyl, 2-methyl-4,6-diisopropylindenyl, fluorenyl, 4-methylfluorenyl or 2,7-di-tert-butylfluorenyl.

Examples of particularly preferred organometallic compounds of the formula I are:
bis(dimethylamido){[(tert-butylamido)dimethylsilyl]cyclopentadienyl}molybdenum,
bis(dimethylamido){[(tert-butylamido)diphenylsilyl]cyclopentadienyl}molybdenum,
bis(dimethylamido){[(tert-butylamido)ethylidene]cyclopentadienyl}molybdenum,
bis(dimethylamido){[(tert-butylamido)isopropylidene]cyclopentadienyl}molybdenum,
bis(dimethylamido){[(tert-butylamido)dimethylsilyl]methylcyclopentadienyl}molybdenum,
bis(dimethylamido){[(tert-butylamido)isopropylidene]methylcyclopentadienyl}molybdenum,
bis(dimethylamido){[(tert-butylamido)dimethylsilyl]tert-butylcyclopentadienyl}molybdenum,
bis(dimethylamido){[(tert-butylamido)diphenylsilyl]tert-butylcyclopentadienyl}molybdenum,
bis(dimethylamido){[(tert-butylamido)ethylidene]tert-butylcyclopentadienyl}molybdenum,
bis(dimethylamido){[(tert-butylamido)isopropylidene]tert-butylcyclopentadienyl}molybdenum,
bis(dimethylamido){[(tert-butylamido)dimethylsilyl]indenyl}molybdenum,
bis(dimethylamido){[(tert-butylamido)diphenylsilyl]indenyl}molybdenum,
bis(dimethylamido){[(tert-butylamido)ethylidene]indenyl}-molybdenum,
bis(dimethylamido){[(tert-butylamido)ethylidene]indenyl}-molybdenum,
bis(dimethylamido){[(tert-butylamido)dimethylsilyl]2-methyl-4-phenylindenyl}molybdenum,
bis(dimethylamido){[(tert-butylamido)dimethylsilyl]2-methyl-4,5-benzoindenyl}molybdenum,
bis(dimethylamido){[(tert-butylamido)dimethylsilyl]fluorenyl}molybdenum,
bis(dimethylamido){[(tert-butylamido)ethylidene]-fluorenyl}molybdenum,
bis(dimethylamido){[(tert-butylamido)isopropylidene]-fluorenyl}molybdenum,
bis(dimethylamido){[(phenylamido)dimethylsilyl]cyclopentadienyl}molybdenum,
bis(dimethylamido){[(phenylamido)dimethylsilyl]methylcyclopentadienyl}molybdenum, bis(dimethylamido){[(phenylamido)dimethylsilyl]tert-butylcyclopentadienyl}molybdenum, bis(dimethylamido){[(phenylamido)diphenylsilyl]indenyl}-molybdenum, bis(dimethylamido){[(cyclohexylamido)dimethylsilyl]cyclopentadienyl}molybdenum, bis(dimethylamido){[(cyclohexylamido)isopropylidene]methylcyclopentadienyl}molybdenum, bis(dimethylamido){[(cyclohexylamido)dimethylsilyl]tert-butylcyclopentadienyl}molybdenum, bis (dimethylamido){[(cyclohexylamido)isopropylidene]-indenyl}molybdenum, bis(dimethylamido){[(cyclohexylamido)dimethylsilyl]fluorenyl}molybdenum, bis(dimethylamido)[bis(cyclopentadienyl)isopropylidene]-molybdenum, bis(dimethylamido)[(cyclopentadienyl)(indenyl)isopropylidene]molybdenum, bis(dimethylamido)[(cyclopentadienyl)(fluorenyl)isopropylidene]molybdenum.

The present invention also provides a process for preparing an organometallic compound of the formula I, which comprises reacting a compound of the formula II, where L is a π ligand, T is a bridge and A is a π ligand or another electron donor, with a compound of the formula III, where M is chromium, molybdenum or tungsten and $R^1$ are, independently of one another, identical or different $C_1$–$C_{20}$-hydrocarbon radicals such as $C_1$–$C_{10}$-alkyl or $C_6$–$C_{14}$-aryl or hydrogen.

The reaction is preferably carried out in an aprotic solvent, e.g. ether. The temperature can be between –78° and 140° C., preferably from 0° to 40° C. The compound of the formula II and the compound of the formula III are preferably used in equimolar amounts. The compound of the formula III can also be used in excess, since unreacted metal amide of the formula III can easily be removed by sublimation.

The methods of preparing compounds of the formula II are known (Chem. Ber. 1990, 123, 1649). The methods of preparing compounds of the formula III are likewise known (J. Chem. Soc. A, (1971), 2741).

Organometallic compounds of the formula I are, in combination with a cocatalyst, suitable catalysts for the polymerization of olefins for preparing olefin polymers.

The present invention thus also provides a process for preparing a polyolefin by polymerization of at least one olefin in the presence of a catalyst, wherein the catalyst comprises at least one organometallic compound of the formula I and at least one cocatalyst. The polymerization can be a homopolymerization or a copolymerization.

Preference is given to homopolymerizing or copolymerizing olefins of the formula $R^a$—CH=CH—$R^b$, where $R^a$ and $R^b$ are identical or different and are each a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins such as ethylene, propylene, 1-butene, 1-pentene, 1-hexene, 4-methyl-1-pentene or 1-octene, styrene, dienes such as 1,3-butadiene or 1,4-hexadiene and cyclic olefins such as norbornene, tetracyclododecene, norbornadiene or vinylnorbornene. In the process of the invention, preference is given to homopolymerizing ethylene or propylene, or copolymerizing ethylene with one or more 1-olefins having 3–20 carbon atoms, for example propylene, and/or one or more dienes having 4–20 carbon atoms, for example 1,4-butadiene. Examples of such copolymers are ethylene-propylene copolymers and ethylene-propylene-1,4-hexadiene copolymers.

The polymerization is preferably carried out at a temperature of from –60° to 250° C., particularly preferably from 50° to 200° C. The pressure is preferably from 0.5 to 2000 bar, particularly preferably from 5 to 64 bar.

The polymerization can be carried out in solution, in bulk, in suspension or in the gas phase, continuously or batchwise, and in one or more stages. A preferred embodiment is gas-phase polymerization.

The catalyst used in the process of the invention preferably comprises one organometallic compound of the formula I. It is also possible to use mixtures of two or more organometallic compounds of the formula I, or mixtures of organometallic compounds of the formula I with other metallocenes, semi-sandwich compounds or classic Ziegler-Natta catalysts, e.g. for preparing polyolefins having a broad or multimodal molecular weight distribution.

In principle, a suitable cocatalyst in the process of the invention is any compound which, owing to its Lewis acidity, can convert the neutral metallocene into a cation and stabilize the latter ("labile coordination"). Furthermore, the cocatalyst or the anion formed therefrom should undergo no further reactions with the metallocene cation formed (EP 427 697). As cocatalyst, preference is given to using an aluminium compound and/or a boron compound.

The boron compound preferably has the formula $R^5_x NH_{4-x} BR^6_4$, $R^5_x PH_{4-x} BR^6_4$, $R^5_3 CBR^6_4$ or $BR^6_3$, where x is a number from 1 to 4, preferably 3, the radicals $R^5$ are identical or different, preferably identical, and are $C_1$–$C_{10}$-alkyl or $C_6$–$C_{18}$-aryl, or two radicals $R^5$ together with the atoms connecting them form a ring, and the radicals $R^6$ are identical or different, preferably identical, and are $C_6$–$C_{18}$-aryl which can be substituted by alkyl, haloalkyl or fluorine. In particular, $R^5$ is ethyl, propyl, butyl or phenyl and $R^6$ is phenyl, pentafluorophenyl, 3,5-bistrifluoromethylphenyl, mesityl, xylyl or tolyl (EP 277 003, EP 277 004 and EP 426 638).

The cocatalyst used is preferably an aluminium compound such as aluminoxane and/or an aluminium alkyl.

The cocatalyst used is particularly preferably an aluminoxane, in particular of the formula IIa for the linear type and/or the formula IIb for the cyclic type,

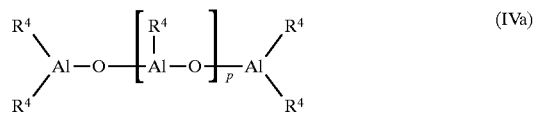

where, in the formulae IVa and IVb, the radicals $R^4$ are identical or different and are each hydrogen or a $C_1$–$C_{20}$-hydrocarbon group such as a $C_1$–$C_{18}$-alkyl group, a $C_6$–$C_{18}$-aryl group or benzyl, and p is an integer from 2 to 50, preferably from 10 to 35.

The radicals $R^4$ are preferably identical and are hydrogen, methyl, isobutyl, phenyl or benzyl, particularly preferably methyl.

If the radicals $R^4$ are different, they are preferably methyl and hydrogen or alternatively methyl and isobutyl, with hydrogen or isobutyl preferably being present in a proportion of from 0.01 to 40% (of the radicals $R^4$).

Methods of preparing the aluminoxanes are known (DE 4 004 477).

The exact spatial structure of the aluminoxanes is not known (J. Am. Chem. Soc. (1993) 115, 4971). For example, it is conceivable that chains and rings are joined to form larger two-dimensional or three-dimensional structures.

Regardless of the method of preparation, all aluminoxane solutions have in common a varying content of unreacted aluminium starting compound, which is present in free form or as adduct.

It is possible to preactivate the organometallic compound of the invention prior to use in the polymerization reaction by means of a cocatalyst, in particular an aluminoxane. This significantly increases the polymerization activity. The preactivation of the organometallic compound is preferably carried out in solution. For this purpose, the organometallic compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but is preferably used in an amount of $10^{-4}$–1 mol per mol of aluminoxane. The preactivation time is from 5 minutes to 60 hours, preferably from 5 to 60 minutes. The preactivation is carried out at a temperature of from −78° to 100° C., preferably from 0° to 70° C.

Here, the organometallic compound is preferably used in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane is preferably used in a concentration of from $10^{-6}$ to $10^{-1}$ mol, preferably from $10^{-5}$ to $10^{-2}$ mol, per $dm^3$ of solvent or per $dm^3$ of reactor volume. The other cocatalysts mentioned are used in approximately equimolar amounts to the organometallic compound. However, higher concentrations are also possible in principle.

To remove catalyst poisons present in the olefin, purification using an aluminium compound, preferably an aluminium alkyl such as trimethylaluminium or triethylaluminium, is advantageous. This purification can be carried out either in the polymerization system itself, or the olefin is, prior to addition to the polymerization system, brought into contact with the aluminium compound and subsequently separated off again.

As molecular weight regulator and/or for increasing the activity, it is possible to add hydrogen in the process of the invention. This enables low molecular weight polyolefins such as waxes to be obtained.

In the process of the invention, the organometallic compound is preferably reacted with the cocatalyst outside the polymerization reactor in a separate step using a suitable solvent. Application to a support can be carried out during this step.

A prepolymerization can be carried out in the process of the invention by means of the organometallic compound. For the prepolymerization, preference is given to using the (or one of the) olefin(s) used in the polymerization.

The catalyst used in the process of the invention can be supported. The application to a support allows, for example, the particle morphology of the polyolefin prepared to be controlled. Here, the organometallic compound can be reacted first with the support and subsequently with the cocatalyst. However, the cocatalyst can also first be supported and subsequently reacted with the organometallic compound. It is also possible to support the reaction product of organometallic compound and cocatalyst. Suitable support materials are, for example, silica gels, aluminium oxides, solid aluminoxane or other inorganic support materials such as magnesium chloride. Another suitable support material is a polyolefin powder in finely divided form. The preparation of the supported cocatalyst can be carried out, for example, as described in EP 567 952.

If the polymerization is carried out as a suspension or solution polymerization, an inert solvent customary for the Ziegler low-pressure process is used. For example, the polymerization is carried out in an aliphatic or cycloaliphatic hydrocarbon; examples which may be mentioned are propane, butane, hexane, heptane, isooctane, cyclohexane, methylcyclohexane. A petroleum or hydrogenated diesel oil fraction can also be used. It is also possible to use toluene. The polymerization is preferably carried out in the liquid monomer.

If inert solvents are used, the monomers are metered in in gaseous or liquid form.

The polymerization time can be any desired, since the catalyst system to be used in the process of the invention has only a slight time-dependent decrease in the polymerization activity.

The polymers prepared by the process of the invention are suitable, in particular, for producing shaped bodies such as films, plates or large hollow bodies (e.g. pipes).

The examples below illustrate the invention:

All glass apparatus was baked out in vacuo and flushed with argon. All operations were carried out with exclusion of moisture and oxygen in Schlenk vessels. The solvents used were distilled under argon from an Na/K alloy.

1. Bis(dimethylamido){[(phenylamido)dimethylsilyl]cyclopentadienyl}molybdenum 1:

$Mo(N(CH_3)_2)_4$ (200 mg, 0.74 mmol) is dissolved in 10 ml of $Et_2O$ and the violet solution is cooled to −78° C. Dimethyl (cyclopentadienyl)(aminophenyl) silane (158 mg, 0.74 mmol) dissolved in 15 ml of $Et_2O$ is slowly added. The reaction mixture is slowly warmed to room temperature and is stirred overnight at this temperature. The dark red solution is heated under reflux for 2 hours, subsequently filtered and the solvent is removed under reduced pressure. Pentane (about 1 ml) is added and the solution is recrystallized at −78° C. 160 mg (60% yield) of a brown solid are isolated.

$^1$H-NMR (400 MHz, $C_6D_6$, 25° C., TMS): δ=0.25 (s, 6H; $Si(CH_3)_2$), 3.20 (s, 12H; $N(CH_3)_2$), 4.88 (t, 2H, $^3J(H,H)$=2.1 Hz, $C_5H_4$), 6.04 (t, 2H, $^3J(H,H)$=2.1 Hz, $C_5H_4$), 6.84 (t, 1H, $^3J(H,H)$=7.1 Hz, para-$C_6H_5$), 7.07 (d, 2H, $^3J(H,H)$=8.6 Hz, ortho-$C_6H_5$), 7.23 (t, 2H, $^3J(H,H)$=8.0 Hz, meta-$C_6H_5$).

2. Bis(dimethylamido){[(tert-butylamido)dimethylsilyl]indenyl}molybdenum 2:

The preparation is carried out by a method similar to Example 1.

$^1$H-NMR (400 MHz, $C_6D_6$, 25° C., TMS): δ=0.28(s, 6H; $Si(CH_3)_2$), 1.14 (s, 9H; $C(CH_3)_3$), 3.26 (s, 12H; $N(CH_3)_2$), 4,79 (d, 1H, $^3J(H,H)$=2.5 Hz, $C_9H_6$), 6.06 (d, 1H, $^3J(H,H)$=2.5 Hz, $C_9H_6$), 6.87 (t, 1H, $^3J(H,H)$=7.0 Hz, $C_9H_6$), 6.95 (t, 1H, $^3J(H,H)$=7.2 Hz, $C_9H_6$), 7.27 (d, 1H, $^3J(H,H)$=7.9 Hz, $C_9H_6$), 7.65 (d, 1H, $^3J(H,H)$=7.9 Hz, $C_9H_6$).

3. Bis(dimethylamido)[(cylopentadienyl)(fluorenyl)isopropylidene]molybdenum 2:

The preparation is carried out by a method similar to Example 1.

$^1$H-NMR (400 MHz, $C_6D_6$, 25° C., TMS): δ=0.58 (s, 6H; $C(CH_3)_2$), 2.95 (s, 12H; $N(CH_3)_3$), 5.21 (t, 2H; $^3J(H,H)$=2.4 Hz, $C_5H_4$), 5.59 (t, 2H, $^3J(H,H)$=2.4 Hz, $C_5H_4$), 7.21 (t, 2H, $^3J(H,H)$=6.9 Hz, $C_{13}H_8$), 7.49 (d, 2H, $^3J(H,H)$=6.7 Hz, $C_{13}H_8$), 7.60 (d, 1H, $^3J(H,H)$=6.8 Hz, $C_{13}H_8$), 7.65 (d, 2H, $^3J(H,H)$=7.0 Hz, $C_{13}H_8$); MS (CI): m/e (%)=456.3 (100) [M$^+$].

We claim:

1. An organometallic compound of the formula I

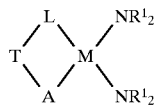

where M is chromium, molybdenum or tungsten, L is a cyclopentadienyl group, T is a bridge, A is a cyclopentadienyl group or an electron donor and $R^1$ are, independently of one another, identical or different $C_1$–$C_{20}$-hydrocarbon radicals or hydrogen.

2. An organometallic compound as claimed in claim 1 where A is a cyclopentadienyl group.

3. The organometallic compound as claimed in claim 1, wherein L is a substituted or unsubstituted cyclopentadienyl group and A is a substituted or unsubstituted cyclopentadienyl group and wherein said substituents are alkyl or aryl or said substituted cyclopentadienyl group is a fluorenyl, alkyl substituted fluorenyl, indenyl, aryl substituted indenyl, alkyl substituted indenyl or alkyl substituted aryl indenyl.

4. The organometallic compound as claimed in claim 3, wherein $R^1$ is identical and are each hydrogen or a $C_1$–$C_{10}$ alkyl or $C_6$–$C_{16}$ aryl.

5. The organometallic compound as claimed in claim 1, wherein L is an unsubstituted cyclopentadienyl, tetramethylcyclopentadienyl, methylcyclopentadienyl, methyl-tert-butylcyclopentadienyl, tert-butylcyclopentadienyl, isopropylcyclopentadienyl, dimethylcyclopentadienyl, trimethylcyclopentadienyl, trimethylethylcyclopentadienyl, 5-phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthylindenyl, 2-methyl-4-isopropylindenyl, benzoindenyl, 2-methyl-4,5-benzoindenyl, 2-methyl-α-acenaphthindenyl, 2-methyl-4,6-diisopropylindenyl, fluorenyl, 4-methylfluorenyl or 2,7-di-tert-butylfluorenyl.

6. The organometallic compound as claimed in claim 5, wherein T is dimethylsilanediyl, methylphenylsilanediyl, diphenylsilanediyl, dimethylgermanediyl, 1,2-tetramethyldisilanediyl, 1,2-ethylidene, 1,2-propylidene, 1,2-butylidene, 1,3-propylidene, or 1,4butylidene.

7. The organometallic compound as claimed in claim 5, wherein M is molybdenum.

8. The organometallic compound as claimed in claim 1 wherein A is tert-butylamido, cyclohexylamido, phenylamido, 2,6-diisopropylphenylamido, 2,6-di-tert-butylphenylamido, cyclododecylamido, —O—, cyclopentadienyl, indenyl, fluorenyl, cyclopentadienyl, tetramethylcyclopentadienyl, methylcyclopentadienyl, methyl-tert-butylcyclopentadienyl, tert-butylcyclopentadienyl, isopropylcyclopentadienyl, dimethylcyclopentadienyl, trimethylcyclopentadienyl, trimethylethylcyclopentadienyl, phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4 -isopropylindenyl, benzoindenyl, 2-methyl-4,5-benzoindenyl, 2-methyl-α-acenaphthindenyl, 2 -methyl-4,6-diisopropylindenyl, fluorenyl, 4-methylfluorenyl or 2,7-di-tert-butylfluorenyl.

9. The organometallic compound as claimed in claim 1, wherein said organometallic compound of formula I is bis(dimethylamido){[(tert-butylamido)dimethylsilyl] cyclopentadienyl}molybdenum, bis(dimethylamido){[(tert-butylamido)diphenylsilyl] cyclopentadienyl}molybdenum, bis(dimethylamido){[(tert-butylamido)ethylidene] cyclopentadienyl}molybdenum, bis(dimethylamido){[(tert-butylamido)isopropylidene] cyclopentadienyl}molybdenum, bis(dimethylamido){[(tert-butylamido)dimethylsilyl] methylcyclopentadienyl}molybdenum, bis(dimethylamido){[(tert-butylamido)isopropylidene] methylcyclopentadienyl}molybdenum, bis(dimethylamido){[(tert-butylamido)dimethylsilyl]tert-butylcyclopentadienyl}molybdenum, bis(dimethylamido){[(tert-butylamido)diphenylsilyl]tert-butylcyclopentadienyl}molybdenum, bis(dimethylamido){[(tert-butylamido)ethylidene]tert-butylcyclopentadienyl}molybdenum, bis(dimethylamido){[(tert-butylamido)isopropylidene] tert-butylcyclopentadienyl}molybdenum, bis(dimethylamido){[(tert-butylamido)dimethylsilyl] indenyl}molybdenum, bis(dimethylamido){[(tert-butylamido)diphenylsilyl] indenyl}molybdenum, bis(dimethylamido){[(tert-butylamido)ethylidene] indenyl}-molybdenum, bis(dimethylamido){[(tert-butylamido)ethylidene] indenyl}-molybdenum, bis(dimethylamido){[(tert-butylamido)dimethylsilyl]2-methyl-4-phenylindenyl}molybdenum, bis(dimethylamido){[(tert-butylamido)dimethylsilyl]2-methyl-4,5-benzoindenyl}molybdenum, bis(dimethylamido){[(tert-butylamido)dimethylsilyl] fluorenyl}molybdenum, bis(dimethylamido){[(tert-butylamido)ethylidene]-fluorenyl}molybdenum, bis(dimethylamido){[(tert-butylamido)isopropylidene]-fluorenyl}molybdenum, bis(dimethylamido){[(phenylamido)dimethylsilyl] cyclopentadienyl}molybdenum, bis(dimethylamido){[(phenylamido)dimethylsilyl] methylcyclopentadienyl}molybdenum, bis(dimethylamido){[(phenylamido)dimethylsilyl]tert-butylcyclopentadienyl}molybdenum, bis (dimethylamido){[(phenylamido)diphenyl-silyl] indenyl}molybdenum, bis(dimethylamido){[(cyclohexylamido)dimethylsilyl] cyclopentadienyl}molybdenum, bis(dimethylamido){[(cyclohexylamido)isopropylidene] methylcyclopentadienyl}molybdenum, bis(dimethylamido){[(cyclohexylamido)dimethylsilyl] tert-butylcyclopentadienyl}molybdenum, bis(dimethylamido){[(cyclohexylamido)isopropylidene]-indenyl}molybdenum, bis(dimethylamido){[(cyclohexylamido)dimethylsilyl] fluorenyl}molybdenum, bis(dimethylamido)[bis (cyclopentadienyl) isopropylidene]-molybdenum, bis(dimethylamido)[(cyclopentadienyl)(indenyl) isopropylidene]molybdenum or bis(dimethylamido)[(cyclopentadienyl)(fluorenyl) isopropylidene]molybdenum.

10. An organometallic compound as claimed in claim 1, where T is a bridge $(R^2{}_2B')_n$, where B' is carbon, silicon or germanium and the radicals $R^2$ are identical or different and are each hydrogen or a $C_1$–$C_{30}$-hydrocarbon radical and n is 1 to 4.

11. A process for preparing an organometallic compound of the formula I,

  (I)

where M is chromium, molybdenum or tungsten, L is a cyclopentadienyl group, T is a bridge, A is a cyclopentadienyl group or an electron donor and $R^1$ are, independently of one another, identical or different $C_1$–$C_{20}$-hydrocarbon radicals or hydrogen, which comprises reacting a compound of the formula II

  (II)

where L is a cyclopentadienyl group, T is a bridge and A is a cyclopentadienyl group or an electron donor, with a compound of the formula III

  (III), where M is a tetravalent metal and $R^1$ is a $C_1$–$C_{20}$-hydrocarbon radical.

12. The process as claimed in claim 11, wherein L is a substituted or unsubstituted cyclopentadienyl group and A is a substituted or unsubstituted cyclopentadienyl group and where T is a bridge $(R^2{}_2B')_n$, where B' is carbon, silicon or germanium and the radicals $R^2$ are identical or different and are each hydrogen or a $C_1$–$C_{30}$-hydrocarbon radical and n is 1 to 4.

13. The process as claimed in claim 12, wherein M is molybdenum.

14. The process as claimed in claim 11, wherein the compound of the formula I is bis(dimethylamido){[(tert-butylamido)dimethylsilyl] cyclopentadienyl}molybdenum, bis(dimethylamido{[(tert-butylamido)diphenylsilyl] cyclopentadienyl}molybdenum, bis(dimethylamido){[(tert-butylamido)ethylidene] cyclopentadienyl}molybdenum, bis(dimethylamido){[(tert-butylamido)isopropylidene] cyclopentadienyl}molybdenum, bis(dimethylamido){[(tert-butylamido)dimethylsilyl] methylcyclopentadienyl}molybdenum, bis(dimethylamido){[(tert-butylamido)isopropylidene] methylcyclopentadienyl}molybdenum, bis(dimethylamido){[(tert-butylamido)dimethylsilyl]tert-butylcyclopentadienyl}molybdenum, bis(dimethylamido){[(tert-butylamido)diphenylsilyl]tert-butylcyclopentadienyl}molybdenum, bis(dimethylamido){[(tert-butylamido)ethylidene]tert-butylcyclopentadienyl}molybdenum, bis(dimethylamido){[(tert-butylamido)isopropylidene] tert-butylcyclopentadienyl}molybdenum, bis(dimethylamido){[(tert-butylamido)dimethylsilyl] indenyl}molybdenum, bis(dimethylamido){[(tert-butylamido)diphenylsilyl] indenyl}molybdenum, bis(dimethylamido){[(tert-butylamido)ethylidene] indenyl}-molybdenum, bis(dimethylamido){[(tert-butylamido)ethylidene] indenyl}-molybdenum, bis(dimethylamido){[(tert-butylamido)dimethylsilyl]2-methyl-4-phenylindenyl}molybdenum, bis(dimethylamido){[(tert-butylamido)dimethylsilyl]2-methyl-4,5-benzoindenyl}molybdenum, bis(dimethylamido){[(tert-butylamido)dimethylsilyl] fluorenyl}molybdenum, bis(dimethylamido){[(tert-butylamido)ethylidene]-fluorenyl}molybdenum, bis(dimethylamido){[(tert-butylamido)isopropylidene]-fluorenyl}molybdenum, bis(dimethylamido){[(phenylamido)dimethylsilyl] cyclopentadienyl}molybdenum, bis(dimethylamido){[(phenylamido)dimethylsilyl] methylcyclopentadienyl}molybdenum, bis(dimethylamido){[(phenylamido)dimethylsilyl]tert-butylcyclopentadienyl}molybdenum, bis(dimethylamido){[(phenylamido)diphenyl-silyl] indenyl}-molybdenum, bis(dimethylamido){[(cyclohexylamido)dimethylsilyl] cyclopentadienyl}molybdenum, bis(dimethylamido){[(cyclohexylamido)isopropylidene] methylcyclopentadienyl}molybdenum, bis(dimethylamido){[(cyclohexylamido)dimethylsilyl] tert-butylcyclopentadienyl}molybdenum, bis(dimethylamido){[(cyclohexylamido)isopropylidene]-indenyl}molybdenum, bis(dimethylamido){[(cyclohexylamido)dimethylsilyl] fluorenyl}molybdenum, bis(dimethylamido)[bis (cyclopentadienyl) isopropylidene]-molybdenum, bis(dimethylamido)[(cyclopentadienyl)(indenyl) isopropylidene]molybdenum or bis(dimethylamido)[(cyclopentadienyl)(fluorenyl) isopropylidene]molybdenum.

* * * * *